(12) United States Patent
Sakayori

(10) Patent No.: US 7,141,354 B2
(45) Date of Patent: Nov. 28, 2006

(54) PHOTO RADICAL GENERATOR, PHOTO SENSITIVE RESIN COMPOSITION AND ARTICLE

(75) Inventor: Katsuya Sakayori, Tokyo (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 95 days.

(21) Appl. No.: 10/946,782

(22) Filed: Sep. 22, 2004

(65) Prior Publication Data

US 2005/0119433 A1 Jun. 2, 2005

(30) Foreign Application Priority Data

Sep. 30, 2003 (JP) .............................. 2003-342340

(51) Int. Cl.
*G03C 1/73* (2006.01)
*C08F 116/36* (2006.01)
*C08F 216/36* (2006.01)

(52) U.S. Cl. ................................ 430/281.1; 430/287.1; 430/139; 526/316; 526/346; 526/347.1; 526/319; 526/317.1

(58) Field of Classification Search ................ 526/316, 526/346, 347.1, 319, 317.1; 430/281.1, 287.1, 430/139
See application file for complete search history.

(56) References Cited

OTHER PUBLICATIONS

Allen et al., Journal of Photochemistry and Photobiology A: Chemistry, 126, 135-149 (1999).*
Hu et al., Macromolecules, 31, 322-327(1998).*
Mihara et al., Mol. cryst. Liq. Cryst., 382, 53-64 (2002).*
Allen et al., Journal of Photochemistry and photobiology A: Chemistry, 54, 367-388(1990).*
Subramanian et al., Makromol. Chem., Rapid Commun. 12, 211-214(1991) or Heijl et al. Polymer, 45, 6771-6778(2004).*
Subramanian et al., European polymer Journal, 36, 2343-2350 (2000).*
Balaji et al., Journal of Applied Polymer Science, 86, 1023-1037(2002).*
Ichimura et al., Makromol. Chem. 188, 2983-2993(1987).*
Balaji et al., Reactive & Functional Polymers, 56, 45-57(2003).*
Balaji et al., Reactive & Functional Polymers, 49, 77-86(2001).*
Lukac et al., Macromol. Chem. Phys., 195, 2233-2245(1994).*
Angiolini et al., Polymer, 35, 5758-5764(1994).*
Goretzki et al., Macromol. Chem. Phys., 198, 59-69(1997).*
Goretzki et al., Macromolecular Reports, A32 (suppls. 1& 2), 237-245(1995).*
Allen et al., Eur. Polym. J., 29, 533-538(1993).*

* cited by examiner

*Primary Examiner*—Ling-Sui Choi
(74) *Attorney, Agent, or Firm*—Timothy J. Keefer; Seyfarth Shaw LLP

(57) ABSTRACT

The invention provides a radical generator, although being a self-cleavage type initiator, which is capable of suppressing volatilization of low molecular weight decomposition materials at the time of light radiation and post-baking, and leaving no low molecular weight decomposition materials in the final product, a photosensitive resin composition and an article using the radical generator. The photoradical generator provided according to the invention contains a compound (a) having one or more self-cleavage type radical-generating parts and one or more ethylenic unsaturated groups in one molecule.

6 Claims, No Drawings

PHOTO RADICAL GENERATOR, PHOTO SENSITIVE RESIN COMPOSITION AND ARTICLE

BACKGROUND OF THE INVENTION

1. Field of the Invention

The present invention relates to a photoradical generator comprising a compound comprising molecular structure having self-cleavage type radical-generating parts and ethylenic unsaturated groups, a photosensitive resin composition containing the generator, and an article produced from the resin composition.

Particularly, the invention relates firstly to a photoradical generator which itself has a function as a photoradical initiator and a function as a polymerizable compound and a self-cleavage type high reaction potential (high sensitivity) as well as fixation capability of the cleavage parts of the photoradical initiator in a matrix and is excellent in compatibility with monomer components.

Secondarily, the invention relates to a photosensitive resin composition containing the radical generator and being capable of decreasing the odor (outgas) at the time of exposure or post-baking and lessening volatile low molecular weight decomposition materials, particularly odorous components, remaining in a product after curing.

Thirdly, the invention relates to an article of which at least a portion is made of the cured product of the photosensitive resin composition and which has high heat resistance and stability so as to be scarcely deteriorated with heat.

2. Description of the Related Art

Photosensitive resins to be cured or to have solubility by light irradiation of UV rays or the like are generally classified into two types; those having exposed parts with good solubility (positive type) and those having unexposed parts with good solubility (negative type). In the case of the negative type, since the photosensitive resins themselves are cured and become insoluble by exposure, the photosensitive resins themselves often remain on substrates to from portions of products as functional films.

Although the negative type photosensitive resin has been used for, for example, paints, printing inks, overcoat layers, adhesives, printing master plates or the like, it has been recently used in wide applications ranging to products such as solder resists for wire protection in printed wiring boards, layer insulation films and resists for forming pixels in color filters, antireflection films, hologram or the like.

One of generally popular negative type photosensitive resins includes a resin composition containing a compound having one or more ethylenic unsaturated bonds, a photoradical initiator for generating radicals by light irradiation, and if necessary, a macro molecular compound, an inorganic filler, a pigment or the like for providing developing ability and softness of coating layer. When light is irradiated to the composition, the molecules of the compound having the ethylenic unsaturated bonds are bonded by radical reaction to increase the molecular weight and be cured. At the time of the curing reaction, three-dimensional mesh structure is developed by the crosslinking reaction, so that the hardness, strength, adhesion property, solvent resistance, and heat resistance of the cured product to be obtained are increased.

Photoradical initiators are broadly classified into self-cleavage type (Type I), and non-self-cleavage type (Type II) (Photocuring technology, p. 39, Technical Information Institute Co., Ltd., 2000). In the case of the former, just like a benzoin ether type compound, the bonds at the positions corresponding to light with specified wavelength are cut by absorbing the light and radicals are generated at the respective cut positions at the moment and there radical reaction starts. In the case of the latter, such a radical initiator has a radical generation mechanism for generating radicals without decomposition at the time of absorption of light with the specified wavelength and, for example, in the case of a hydrogen-drawing type represented by benzophenone, it absorbs electromagnetic wave with specified wavelength and when elevated to excited state, it draws hydrogen from hydrogen donors in the surrounding and at that moment, radicals are generated in both of the drawing side and the drawn side.

In general, self-cleavage type radical initiators are good in the sensitivity and radical generation efficiency, however generate low molecular decomposition materials at the time of light irradiation and such low molecular decomposition materials cause odor by volatilization in the work environments or are condensed again after volatilization to result in pollution of production apparatus and inferior product production, or such low molecular decomposition materials remain in products to deteriorate heat resistance and stability of the products or are slowly released from the products.

On the other hand, the hydrogen-drawing type are free from the generation or remaining of the low molecular decomposition materials derived from the initiators, however, they require existence of hydrogen donors in the vicinity of the excited initiators or have relatively low sensitivity since their radical generation efficiency is determined depending on the energy barrier height at the time of drawing of hydrogen.

To say more practically, there may be the following problems of the self-cleavage type initiators to be encountered in the case of various uses.

Firstly, as an example, use for a solder resist or color resist can be exemplified. The solder resist to be used for surface coverage of a printed wiring board contains an organic pigment and a filler for providing heat resistance and flame resistance or the resist for pixel formation for a color filter contains a pigment for color display. Since these pigments are components absorbing light, they utilize mainly self-cleavage type photoradical initiators and are added in large quantities including the amount for vain use in radical reaction of them in order to increase the sensitivity of the photosensitive resins. Here, the portion which is not effectively used in the radical reaction includes the unreacted initiators not cleaved by radiation and those which become inactive by inhibition from the contact with objects to be reacted because of solid-phase reaction even though they become radical by cleavage.

Accordingly, the initiators are used in large quantities, so that large quantities of low molecular decomposition materials are generated at the time of light radiation and odor is emitted. Further, in the cured products after exposure, large quantities of residues derived from the initiators exist and among them, the un-self-cleaved photoradical initiators still keep reactivity even after the exposure and therefore denature the cured products. Also, the un-self-cleaved photoradical initiators and inactivated low molecular decomposition materials which are cleaved but not consumed by the radical reaction are not bonded to the crosslinking structure of the matrix and exist as independent components in the cured products to deteriorate the physical properties. Therefore, if the residues derived from the initiators are left as they are, they worsen the light fastness, colorization or discoloration, separation and cracking of the coating layers and lead to deterioration of the reliability of the final products, for example, interlayer insulating films for electronic parts, solder resist, resist for pixel formation for color filters.

The self-cleavage type photoradical initiator has a strong sublimation tendency and is decomposed by heat. It can be therefore removed from a product by post-baking after exposure and developing at a temperature higher than hundred and several tens degree. However, a large amount of a sublimated material originated from an initiator adheres to the inside of a heater and falls on a product obtained by curing during post-baking, causing product defects, posing a serious problem. Also, a decomposed material of an initiator or the like is involved in the atmosphere around the heater, posing a problem from the viewpoint of operational safety.

It is possible to remove more residues originated from a radical initiator by changing a post-baking condition to a condition of a higher-temperature and longer-operation time. However, it is difficult to remove the residues completely because of volatilization from a solid. If the condition is made stricter to remove many more impurities originated from a radical initiator, this condition rather causes product defects.

Secondary, use of resist for peeling films can be exemplified. Similarly to that of the above-mentioned solder resist, resist for processing electronic members, dry film resist or the like to be used for peeling films employ the photocuring system. The resists for processing are peeled and do not remain in the products finally, however, in the processing steps of copper wiring formation, the residues derived from the initiators from the resist films are eluted in chemical solutions such as ferric chloride, cupric chloride or the like to be used for the processing to shorten the chemical solution life.

Moreover, thirdly, use for coating material for protecting films can be exemplified. When a photosensitive resin is used as a wall used for buildings or paint for a protective layer protecting a surface of wall paper, there is a demand for decreasing solvent components or odorous components emitting from whole building material with the view of dealing with sick house syndrome. There is a problem that the use of a highly volatile initiator causes the occurrence of odors even after curing.

As one of the means for solving the above-mentioned problems, ESACURE KIP 150 (trade name) is commercialized by Nihon Siber Hegner K.K. The ESACURE KIP 150 has a structure in which photoradical generation portions are introduced in the side chains of the polymer skeleton. With such a structure, the photoradical generator has a plurality of radical generation portions in one molecule and therefore, if any one portion of the molecule is made radical and bonded with the matrix of the coating layer, the unreacted radical generation portions existing in the same molecule are bonded to the matrix structure and thus are not volatilized in post-baking and do not move in the coating layers to scarcely deteriorate the reliability of the final products.

However, ESACURE KIP 150 has a polymer skeleton with relatively large molecular size and therefore is difficult to move in a photosensitive resin composition. Further, the sensitive wavelength is not matched with the radiation wavelength of common light sources. Therefore, the sensitivity in the resin composition is not so high in practical use and the photoradical reactivity is hard to be increased.

As another solution, LUNA 750 (trade name) is commercialized by Nihon Siber Hegner K.K. The LUNA 750 is produced by introducing functional groups (side chains) with high molecular weight into self-cleavage type radical-generating parts having α-aminoacetophenone skeleton to increase the molecular weight of the parts to be isolated by cleavage at the time of radical generation and thus volatilization (outgas) of decomposition materials can be suppressed. However, in this case, the molecular weight in the cleaved parts is increased only to increase the temperature of the volatilization and make gasification difficult, the decomposition materials independent from the matrix structure of the coating layer remain in the coating layer. Therefore, it cannot sufficiently solve the problems of reliability deterioration, e.g. inferior products owing to the decomposition materials, occurrence of volatilization, elution, and odor emission of the decomposition materials, of the final products of coating layers or the like. Also, it cannot deal with the problem of elution of decomposition materials or unreacted materials derived from the initiators to developers or washing solutions in the case of development or washing intermediate products and final products.

SUMMARY OF THE INVENTION

It is an object of the present invention to solve the above-mentioned problems which a self-cleavage type photoradical generator has. More particularly, the first object of the present invention is to provide a radical generator having sensitivity as high as that of a conventional self-cleavage type initiator and capable of suppressing volatilization of low molecular weight decomposition materials and odor emission from resin composition or an intermediate product at the time of light irradiation or post-baking and leaving practically no low molecular weight decomposition material independent from the matrix of a cured product in the final product after photocuring.

The second object of the present invention is to provide a photosensitive resin composition containing the above-mentioned radical generator and scarcely evaporating low molecular weight decomposition materials and generating odor at use and leaving little residues of the low molecular weight decomposition materials in the final product after photocuring.

The third object of the present invention is to provide an article hardly deteriorated by heat and having high heat resistance and stability and comprising at least a portion formed by using the above-mentioned photosensitive resin composition.

To solve the above-mentioned problems, a photoradical generator produced according to the invention contains a compound (a) having one or more self-cleavage type radical-generating parts and one or more ethylenic un saturated groups in one molecule.

The photoradical generator of the present invention has a function as a self-cleavage type radical generator and a function as a curable reactive compound.

When light is irradiated to the photoradical generator of the present invention, the self-cleavage type radical-generating parts are cleaved to generate radicals. The segments produced at that time have ethylenic unsaturated groups, so that they are bonded to and fixed in a matrix structure of the cured product by polymerization reaction of the ethylenic unsaturated groups. Accordingly, the production amount of the low molecular weight decomposition materials existing independently form the matrix of the cured product is slight.

Accordingly, the amount of the low molecular weight decomposition materials volatilized at the time of light irradiation or post-baking is considerably decreased and particularly odor is lessened. Also, the amount of decomposition materials to be deposited on a production apparatus or a product by re-condensation after volatilization or the amount of decomposition materials to be eluted to a development solution or a washing solution is considerably decreased. Further, the amount of low molecular weight decomposition materials remaining after the curing is decreased to remarkably improve the heat resistance and stability of the final product.

The molecular size of the photoradical generator of the present invention before radical reaction is much smaller than those of polymers. Therefore, the photoradical generator has high compatibility with and solubility in monomer components and other components such as solvents and relatively easily and freely moves in a photosensitive resin composition. Accordingly, it has sensitivity as high as those of conventional self-cleavage type photoradical generators.

Next, a photosensitive resin composition according to the invention contains the above-mentioned photoradical generator of the present invention as an essential component.

When the resin composition of the present invention is applied in prescribed patterns or formed in a prescribed shape and subjected to light irradiation, photoradical reaction is started and various radical reactions such as radical polymerization are promoted to cure the composition and/or change the solubility. At the radical reaction, the photoradical generator containing the compound (a) works as a self-cleavage type radical generator to efficiently generate radicals to provide high sensitivity.

Further, at least one of segments produced by the cleavage of the compound (a) is bonded to the matrix of the cured product by the reaction of the ethylenic unsaturated groups to form a portion of the chemical structure of the product. Accordingly, the amount of the low molecular weight decomposition materials derived from the radical generator is extremely decreased as compared with that of the case of using a conventional self-cleavage type radical generator. Subsequently, the amount of the low molecular weight decomposition materials volatilized at the time of exposure or post-baking is considerably decreased and particularly odor is lessened. Also, the problems of re-condensation of the volatilized low molecular weight decomposition materials or elution of them to a development or the like can be improved.

Further, since the amount of low molecular weight decomposition materials remaining in the final product is slight, heat resistance and stability are effectively improved. Accordingly, the problem of reliability decrease of the final product can be solved.

When the photosensitive resin composition is used as a pattern-forming material, a paint or printing ink, or a formation material for a color filter, an electronic part, an interlayer insulation film, a wire cover film, an optical material, an optical circuit, an optical circuit part, an anti-reflection film, a hologram, or a forming material for building material, the product or film is provided with high heat resistance and high stability. Also, since no odor is emitted at the time of exposure, the work environments are improved.

The photoradical generator of the present invention has self-cleavage type high reaction potential and is capable of suppressing production of the low molecular weight decomposition materials. According to the invention, odor emission, which is one of the problems of self-cleavage type radical generators, can be lessened.

Particularly, in the case that a photoradical generator contains an aromatic component such as benzaldehyde said to be a cause of strong odor among odorous components, the aromatic component is fixed in the matrix to remarkably increase the odor lessening effect.

Accordingly, the photoradical generator of the present invention can be used as a photoradical generator for starting and promoting the radical reaction such as radical polymerization by excitation by light radiation.

Also, since the photoradical generator of the present invention has a function as a self-cleavage type radical generator and a function as a polymerizable compound, the photoradical generator itself can be used preferably as a curable reactive component having the photoradical initiation.

Since the photosensitive resin composition of the present invention contains the photoradical generator of the present invention as an initiator, the composition has sufficient sensitivity for practical use and although using the self-cleavage type radical generator, the composition generates little low molecular weight decomposition materials as by-products. Particularly, the composition has a significant effect to decrease odor. Further, since the amount of the low molecular weight decomposition materials remaining in the final product is low, the final product obtained has high heat resistance, high stability and high reliability.

Since a printed matter, a color filter, an electronic part, an interlayer insulating film, a wire cover film, an optical member, an optical circuit, an optical circuit part, an antireflection film, a hologram, or a building material relevant to the invention has at least a portion of a cured product of the photosensitive resin composition with high heat resistance and high stability, such a product or film is provided with high heat resistance and high stability and thus the production yield of the product or film is also increased.

DETAILED DESCRIPTION OF THE PREFERRED EMBODIMENT

Hereinafter, the invention will be described in detail. The radiation light to be used for causing the photoradical generation process in the present invention may include not only visible light and electromagnetic wave with wavelength in non-visible region capable of radicalizing the radical generation positions of the photoradical generator or causing radical reaction of the photosensitive resin composition but also particle beam such as electron beam and radiation beam or ionized radiation ray which is a general term of electromagnetic wave and particle beam. To cure the resin composition, mainly electromagnetic wave with wavelength of 2 μm or shorter, electron beam, and ionized radiation ray or the like may be used.

At first, a photoradical generator of the present invention will be described. The photoradical generator according to the invention comprises a compound (a) having one or more self-cleavage type radical-generating parts and one or more ethylenic unsaturated groups in one molecule.

The above-mentioned compound (a) has one or more self-cleavage type radical-generating parts and one or more ethylenic unsaturated groups in one molecule and has a function as a self-cleavage type radical generator and a function as a curable reactive compound.

The self-cleavage type radical-generating parts of the photoradical generator in the present invention mean parts which are excited by light absorption and generate radicals along with decomposition of the molecular structure (cleavage of the bonding), that is, parts having radical generation mechanism classified in Type I. Examples of the self-cleavage type radical-generating parts are structures formed by removing one or more hydrogen atoms at the positions to be bonded with the ethylenic unsaturated groups from the compounds having radical generation mechanism in Type I such as benzophenone derivatives, benzyl ketals, α-acetoxyphenone, α-aminoacetophenone, acylphosphine oxides, titanocenes, o-acyloxime or the like.

In general, a self-cleavage type photoradical initiator generates low molecular weight decomposition materials by cleavage of molecular structure at the time of radical generation. As one example, α-aminoacetophenone skeleton known as a highly sensitive self-cleavage type photoradical-generating part produces a benzoyl radical and an amino radical when it is excited by light and intermolecular cleavage is caused. The polymerization reaction is supposed to start by drawing hydrogen of an object to be reacted (a raw material compound) by the amino radical or the benzoyl radical.

Principally, the respective radicals are possible to be bonded to the ends of the object at the time of starting polymerization, however, practically, they draw hydrogen from molecules existing in the surrounding to generate radical and become inactive themselves in the cleaved state as they are and tend to be decomposition materials independent from the molecules of the polymer. The low molecular weight decomposition materials produced by the cleavage of the self-cleavage type photoradical-generating parts cause such problems as to emit gases and odor by volatilization at the time of light radiation or post-baking, to deposit on a production apparatus or a product by re-condensation after volatilization or to remain in the final product to deteriorate the heat resistance and stability of the product without being volatilized.

Particularly, the benzoyl radical tends to be benzaldehyde or its analogs by drawing hydrogen of surrounding molecules and is difficult to be bonded to the matrix in the vicinity. Having strong odor, benzaldehyde and its analogs become major causes of odor at the time of light radiation and post-baking and moreover since they are difficult to be volatilized completely at the time of post-baking, they remain in the final product and become causes of odor or deterioration of the product.

On the contrary to such a conventional self-cleavage type photoradical initiator, the compound (a), a photoradical generator of the present invention, has ethylenic unsaturated groups in the portions to be segments by the cleavage of the self-cleavage type photoradical-generating parts. Therefore, if the photoradical reaction is started and promoted by using the compound (a) as the photoradical initiator, the segments produced by the cleavage of the self-cleavage type photoradical-generating parts are bonded to the matrix structure of the cured product through the ethylenic unsaturated groups and fixed therein.

As a result, the amount of the low molecular weight decomposition materials volatilized at the time of light radiation and post-baking is significantly decreased and particularly odor is lessened. The amount of the decomposition materials to deposit on a production apparatus by re-condensation after volatilization or the amount of the decomposition materials to be eluted to a development solution or a washing solution can considerably be decreased. Further, the amount of the low molecular weight decomposition materials remaining after curing is decreased and thus the heat resistance and stability of the final product are remarkably improved.

Also, most of the segments produced by cleavage of the compound (a) are bonded to polymerization or crosslinking matrix structure to form a portion of large molecular weight, however, the molecular size before the radical reaction is much smaller than polymers. Therefore, they have high compatibility with and solubility in monomer components and other components such as solvents and can relatively easily and freely move in a photosensitive resin composition. Accordingly, a resin composition having sensitivity as high as those of conventional self-cleavage type photoradical initiators and sufficient reactivity for practical use can be obtained.

As the compound (a) having one or more self-cleavage type radical-generating parts and one or more ethylenic unsaturated groups in one molecule, for example, a compound (a1) represented by the following formula (1) can be used:

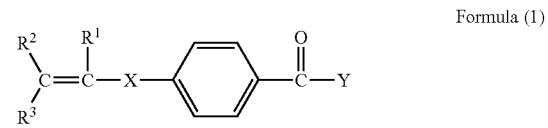

Formula (1)

wherein $R^1$, $R^2$, and $R^3$ respectively represent a hydrogen atom, a halogen atom, or a monovalent organic group; X represents a divalent group; and Y represents a monovalent group.

The compound (a1) has self-cleavage type radical-generating part defined as —(C=O)—Y and generates two radicals by cleavage of the bond between the carbonyl carbon and the monovalent Y group. Between the produced radicals, if the segment having the benzoyl radical structure is inactivated and becomes benzaldehyde or its analogs having independent molecular structure, these compounds are easily volatilized to cause odor. On the other hand, the ethylenic unsaturated group of the compound (a1) is bonded to the portion to be the segment having the benzoyl radical structure, benzaldehyde or its analogous compound structure mainly causing odor are fixed to the matrix structure of the cured product. Accordingly, in this case, the production amount of strongly odorous low molecular weight decomposition materials is suppressed to extremely low to efficiently decrease odor emission.

$R^1$, $R^2$, and $R^3$ existing in the ethylenic unsaturated group of the compound (a1) respectively represent a hydrogen atom, a halogen atom, or a saturated or unsaturated monovalent organic group. The monovalent organic group may contain heteroatom other than carbon and/or substituents. $R^1$, $R^2$, and $R^3$ respectively represent preferably a hydrogen atom, a halogen atom, a saturated or unsaturated alkyl, a saturated or unsaturated halogenated alkyl, or a saturated or unsaturated hydroxyalkyl and particularly preferably a hydrogen atom, a halogen atom, a methyl group, a trifluoromethyl group, or a hydroxymethyl group. Particularly, in terms of the cost, rate of radical reaction, and physical properties of the final coating layer, the ethylenic unsaturated group is most preferably having a hydrogen atom, a halogen atom, a methyl group, a trifluoromethyl group or a hydroxymethyl group for $R^1$ and a hydrogen atom or fluorine atom for $R^2$ and $R^3$, respectively.

Preferable examples of the ethylenic unsaturated group are an acryloyl group, a methacryloyl group, a 2-trifluoromethylacryloyl group and an unsubstituted vinyl group.

In the above formula (1), the monovalent group Y contained in the self-cleavage type photoradical-generating part may have a structure containing, for example, an aliphatic ether or aliphatic amine skeleton and is preferably a group having an aliphatic tertiary amine structure.

The chemical structure "X" bonded to the ethylenic unsaturated group and the self-cleavage type radical-generating part in the formula (1) may be any chemical structure having di- or more valences and typically a divalent organic group having, for example, a chemical structure defined by the following formula (2):

—X2—X1—X3— Formula (2)

In the divalent organic group presented by the above formula (2), X1 represents a divalent organic group, X2 may be a bond possible to be bonded to the ethylenic unsaturated group, and X3 may be a bond possible to be bonded to the benzoyl structure.

The structure of the divalent organic group X1 is not particularly limited. Practically, it is preferably a straight, branched, or cyclic alkylene group having 1 to 15 carbon atoms. Additionally, these saturated alkylene groups may have aliphatic and/or aromatic cyclic parts and/or additional structures composed of one or more bonds in combinations such as ester bond, ether bond, thioether bond, amino bond, amide bond, urethane bond, urea bond, thiocarbamate bond, carbodiimide bond, carbonate bond or the like, in the middle of the carbon skeleton. The divalent organic group X1 may be a polymer chain composed of a certain repeating unit just like a polycaprolactone structure of the like.

The structure X2 possible to be bonded to the ethylenic unsaturated group may include practically a single bond, ester bond, ether bond, thioether bond, amino bond, amide bond, urethane bond, urea bond, thiocarbamate bond, carbodiimide bond, carbonate bond or the like, however, it is not particularly limited if it is a known divalent bond.

In terms of the price and availability and easiness of synthesis, X2 is preferably a single bond, ester bond, ether bond, thioether bond, amino bond, amide bond, urethane bond, urea bond, thiocarbamate bond, carbodiimide bond, carbonate bond or the like.

The structure X3 possible to be bonded to the benzoyl structure may have a similar structure as the above-mentioned structure X2 and is preferably a group adjusting the absorption wavelength of the compound (a1) and increasing the absorption of the radiation wavelength.

A more particular example of the compound categorized in the compound (a1) represented by the formula (1) is compound (a3) represented by the following formula (3):

Formula (3)

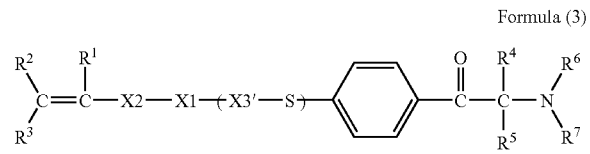

wherein $R^1$, $R^2$, and $R^3$ respectively represent a hydrogen atom, a halogen atom, or a monovalent organic group; $R^4$ and $R^5$ respectively represent a hydrogen atom or an alkyl having 1 to 15 carbon atoms (preferably 1 to 6 carbon atoms); $R^6$ and $R^7$ respectively represent a monovalent organic group and may have hetero atoms such as O, N, S, Si or the like other than C; $R^6$ and $R^7$ may bonded to each other to form a ring structure; X1 represents a divalent organic group; X2 and X3' independently represent a divalent group.

The compound (a3) has a structure comprising S (sulfur) bonded to the para-position of the benzoyl structure and a tertiary amine structure bonded to the carbonyl carbon of the benzoyl structure through a methylene group optionally substituted with alkyl. The structure has high radical generation capability. In general, when an S-containing benzoyl radical becomes inactive and a benzaldehyde analog having independent molecular structure is produced, it is volatilized and emits very strong odor. On the other hand, in the case of using the compound (a3), even if benzoyl radical is generated, the S-containing benzaldehyde analog is not volatilized to significantly suppress odor.

The amino radical produced together with the benzoyl radical has high capability of initiating the radical chain reaction and therefore, in the case that this portion can move freely in the reaction system, particularly high sensitivity can be obtained. In the case of using the compound (a3), since no ethylenic unsaturated group exists in the amino radical, the amino radical can move freely in the photosensitive resin composition. Accordingly, high sensitivity can be obtained.

A more particular example of the compound categorized in the compound (a3) represented by the formula (3) is compound (a4) represented by the following formula (4):

Formual (4)

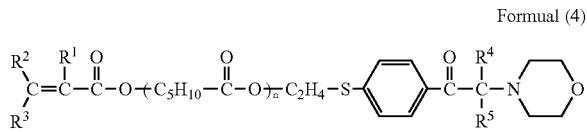

wherein $R^1$ to $R^7$ respectively represent same as those of the formula (3); n is an integer of 0 to 15, more preferably an integer of 0 to 8.

The tertiary amine structure portion of the compound (a4) has a morpholine skeleton. The amino radical produced from the compound becomes morpholine with independent molecular structure or its analog and volatilized when it finally becomes inactive, however, the odor of morpholines is weak as compared with the odor of benzaldehydes. Accordingly, undesirable effects on work environments are scarce. Also, since morpholines have high volatilization property, they can easily be removed from the product in the production process such as light radiation, post-baking or the like and scarcely remain. Consequently, the decomposition materials having morpholine structure scarcely deteriorate the heat resistance, stability, and reliability of the final product.

To improve the radiation sensitivity of the compound (a), which is the photoradical generator of the present invention, it is desirable for the radical generation parts contained in the compound to be excited by radiated light and for the compound to have the chemical structure easy to generate radicals. For that, it is supposed effective to properly select the substituent groups (e.g. the above-mentioned $R^4$ to $R^7$) contained in the compound (a) and the bonding structure (e.g. the above-mentioned X) to shift the light absorption wavelength or change the absorption coefficient.

In order to obtain practical sensitivity, it is preferable to make a selection of the substituent groups and the bonding structure so that a part of the absorption wavelength of the compound (a) overlaps on any of the emitting wavelengths of an exposure light source (irradiation light source) in a process. The absorption maximum of the compound (a) falls within a range of particularly preferably ±20% and still more preferably ±10% of the emitting wavelength closest to the absorption maximum.

The molar extinction coefficient of the compound (a) in any of the emitting wavelengths of an exposure light source (irradiation light source) in a process is preferably 0.1 or more from the viewpoint of sensitivity. Here, the molar extinction coefficient ϵ is given by the relationship induced from the Lambert-Beer rule and expressed by the following formula:

$$A = \epsilon cb$$

where:
- A=Absorbance;
- b=Length of an optical path in an example (cm); and
- c=Concentration of a solute (mol/L).

Generally, when a change in absorbance is recorded using a solution having the same concentration and a cell having the same length of an optical path with changing the wavelength of incident light, the absorbance varies according to the wavelength, showing a maximum molar extinction coefficient $\epsilon_{max}$ at a wavelength specific to a compound to be a subject of measurement. The aforementioned term "the molar extinction coefficient of the above-mentioned compound in the exposure wavelength is 0.1 or more" implies that the molar extinction coefficient when measured using a wavelength adopted when carrying out exposure by using the compound is 0.1 or more but does not imply that the maximum molar extinction coefficient $\epsilon_{max}$ is 0.1 or more.

In the case of a usual high pressure mercury lamp, there are three significant emissions at 365 nm (i rays), 405 nm (h rays) and 436 nm (g rays). However, in actual, emissions are also present at, for instance, 333 nm or the like. Therefore, a photo-crosslinking compound may have absorption maximum in the vicinity of these wavelengths. Also, when irradiating with an F2-excimer laser (157 nm), ArF excimer laser (193 nm), KrF excimer laser (248 nm) or the like, the photo-crosslinking compound may have absorption in the vicinity of these wavelengths. Specifically, the absorption maximum around 365 nm falls in a range of preferably 365±73 nm and more preferably 365±37 nm.

When the absorption wavelength is overlapped with at least one of the regions around 157 nm, 193 nm, 248 nm, 365 nm, 405 nm, and 436 nm, which are main emitting wavelength values of the above-mentioned widely employed exposure light sources, the wavelength is convenient to be used as the exposure wavelength and it is particularly preferable that the molar absorbance coefficient at the wavelength is 0.1 or more.

If the absorption wavelength is overlapped on the region covering at least one wavelength among 157 nm, 193 nm, 248 nm, 365 nm, 405 nm and 436 nm which are major emitting wavelengths of the above-mentioned widely employed exposure light sources, this is convenient to utilize these wavelengths as exposure wavelengths. It is particularly preferable that the molar extinction coefficient at this wavelength is 0.1 or more.

THE INTERPRETATION OF THE ULTRAVIOLET SPECTRA OF NATURAL PRODUCTS (A. I. Scott, 1964) and the table described in THE ORGANIC COMPOUND IDENTIFICATION METHOD BY A SPECTRUM, fifth edition (R. M. Silverstein, 1993) may be used as the references showing a guide to determine as to what substituent is introduced to shift the absorption wavelength to a desired wavelength.

In the case of using the photoradical generator containing the above-mentioned compound (a) of the present invention, the segment generated by the cleavage of the self-cleavage type photoradical-generating parts is bonded to the matrix structure of the cured product through the ethylenic unsaturated group and therefore, low molecular weight decomposition materials with high volatile property and independent from the matrix structure scarcely remain. Accordingly, the stability of the finally obtained cured film is improved and the light-resistance of the coating layer from being impaired and coloring, fading, peeling and cracks of the coating layer can be prevented.

In terms of the heat resistance, the 5% reduction in weight temperature of the photoradical generator according to the invention is preferably 50° C. or more, more preferably 100° C. or more, and even more preferably 130° C. or more.

The 5% reduction in weight temperature means the temperature at the time when the weight of a sample is decreased by 5% from the initial weight in the case that the weight reduction is measured by a thermogravimetric analysis in the same technique as that employed in Example of the present invention described later. Similarly, the 10% reduction in weight temperature means the temperature at the time when the weight of a sample is decreased by 10% from the initial weight.

The above-mentioned photoradical generator is preferable to have high solubility in the case of adding it to a resin composition in terms of the coatability, transparency after curing, and sensitivity at the time of exposure.

In terms of the coatability, the photoradical generator is particularly preferable to have high solubility in a solvent. Practically, the solubility of the photoradical generator in a solvent to be used, particularly, a widely used solvent, which will be described later, is preferably 0.1% by weight or more.

Further, even if a resin composition obtained by dissolution in a solvent is transparent, the compatibility of the contained solids with one another is low, precipitates are formed in the coating layer during drying of the coating layer to make it difficult to obtain sufficient transparency. Therefore, in the case that a coating layer or molded body with high transparency such as an optical member is required, a photoradical generator with high compatibility with other solid components in the resin composition, particularly with the radical reactive compound such as compounds having the ethylenic unsaturated groups, is preferable to be used. When high transparency is required, the all ray-transmittance (JIS K 7105) is preferably 90% or more, more preferably 95% or more, in the case the film thickness of the coating layer formed by curing the resin composition is 10 μm.

When the solubility of the photoradical generator in the radical reactive compound is high, the function as the initiator is improved, so that the sensitivity at the time of exposure is increased high. From that point, in the case the solubility is evaluated by using methyl acrylate as a typical monomer component, the saturation concentration of the photoradical generator in the methyl acrylate at 20° C. is preferably 0.01 mol/L or more.

The solubility or compatibility of the photoradical generator can be improved by properly selecting the substituent groups (e.g. the above-mentioned $R^4$ to $R^7$) or the bonding structure (e.g. the above-mentioned "X") of the compound (a) in consideration of the solvent to be dissolved or other solid components to be compatible with. For example, in the case a carboxyl group is selected as a substituent group, the photoradical generator becomes easy to be dissolved in water and organic polar solvent and in the case that ester is introduced, the solubility in a solvent and a compound having ester bond is improved.

The compound (a), the photoradical generator of the present invention, can be synthesized by various known methods. Examples of such methods are a method of synthesizing a compound having self-cleavage type radical-generating parts at first and then introducing ethylenic unsaturated groups into the compound; and a method of at first introducing ethylenic unsaturated groups into a precursor which can be induced into the structure of the self-cleavage type radical-generating parts and then inducing a portion of the precursor into the self-cleavage type radical-generating parts, however the methods are not particularly limited.

A method of synthesizing a compound represented by the above-mentioned formula (a4) will be exemplified more particularly, however, it is not intended that the invention be limited to the exemplified method.

As a raw material, a self-cleavage type radical generator comprising a substituent group having active hydrogen such as a hydroxyl group, an amino group or the like is used. The above-mentioned active hydrogen is substituted with an ethylenic unsaturated group. Such a raw material is not particularly limited, and a compound obtained by modifying the benzophenone portion of $\alpha$-aminoacetophenone with caprolactone can be used. Those containing one or several caprolactone groups in the caprolactone-modified portion may be used. There is LUNA 750 (product name; manufactured by Nihon Siber Hegner K.K.) made available as a commercialized product of such caprolactone-modified $\alpha$-aminoacetophenone.

Next, the above-mentioned raw material compound and triethylamine are mixed and stirred with dehydrated tetrahydrofuran (THF). Acrylic acid chloride is gradually added to the mixture until no raw material spot of the raw materials is found in the resulting reaction solution by thin layer chromatography and if required, the reaction solution is successively stirred at room temperature for about 1 to 15 hours. The reaction solvent is not limited to the above-mentioned tetrahydrofuran and any solvents such as organic polar solvents or the like in which the final product can be dissolved may be used. If the reaction solvent is dehydrated, the yield is improved and therefore it is preferable.

After the stirring, the reaction solution is moved to a solution filtration funnel and treated with 1N HCl to transfer triethylamine to a water layer. After separation of the water layer and an oil layer, the oil layer is further treated with a saturated $NaHCO_3$ solution to transfer acrylic acid derived from the unreacted acrylic acid chloride to the water layer, thus, the water layer and an oil layer are separated. The separated oil layer is dehydrated by a proper dehydrator such as magnesium sulfate or the like and filtered. The product obtained by distillation removal of the solvent from the obtained filtrate is refined by column chromatography or re-crystallization to obtain an aimed product.

The photoradical generator of the present invention obtained in such a manner has a self-cleavage type high reaction potential (high sensitivity) and also high capability of fixing segments derived from the photoradical initiator in the matrix and excellent solubility in solvents or monomer components, so that it can be used as a photoradical generator for initiating and promoting the radical reaction such as radical polymerization by being excited by light radiation. Since the photoradical generator of the present invention has a function as a self-cleavage type photoradical initiator and a function as a polymerizable compound and therefore is preferably used itself as a curable reactive component having photoradical initiator.

Next, a photosensitive resin composition (hereinafter, simply referred to as resin composition) according to the invention will be described.

The resin composition of the present invention contains the above-mentioned photoradical generator as an essential component, and based on necessity, further a compound (b) having an ethylenic unsaturated group, a radical-reactive compound other than the compound (b) or a curable reactive compound other than the radical-reactive compound, a binder component with high molecular weight, a hydrogen donor, a radical generator other than the compound (a) or other components.

When the resin composition of the present invention is applied in prescribed patterns or formed in a prescribed shape and subjected to light radiation, photoradical reaction starts and various radical reactions such as radical polymerization, radical dimerization, radical crosslinking and the like proceed to cure the composition and/or change the solubility. At the time of the radical reactions, the photoradical generator containing the compound (a) works as the self-cleavage type radical generator to efficiently generate radicals, so that high sensitivity can be obtained. Further, since the compound (a) has at least one ethylenic unsaturated group, at least one of the segments produced by cleavage is bonded to the matrix of the cured product by the reaction of the ethylenic unsaturated group to form a portion of the chemical structure. As a result, the amount of the low molecular weight decomposition materials derived from the radical generator is considerably decreased as compared with that in the case of using a conventional self-cleavage type radical generator. Accordingly, the volatilization amount of the low molecular weight decomposition materials is decreased at the time of exposure and post-baking to lessen odor and suppress re-condensation of the volatilized low molecular weight decomposition materials. Also, since the formed body or coating layer after curing contains a little amount of the low molecular weight decomposition materials existing independently from the matrix, the heat resistance and the stability are heightened. Consequently, the problem of decrease of reliability of the final product can be solved.

Further, since the photoradical generator containing the compound (a) has the ethylenic unsaturated group and works as a radical reactive compound, a resin composition having photo-curability can be obtained without adding other radical reactive compounds.

Here, the crosslinking means that a crosslinking bond is generated, wherein the crosslinking bond means a bond formed in such a manner as to build a bridge between optional two atoms among a molecule consisting of atoms bound chain-wise. The bond in this case may be formed in the same molecule or between different molecules (CHEMICAL HANDBOOK, Tokyo Kagaku Dojin Co., Ltd., p. 1082). The chains may include alicyclic structures.

Conventionally, the compound (b) having the ethylenic unsaturated group has been used popularly as a curable reactive compound which is radically polymerizable in a wide range of uses and is also used preferably in the present invention. As the compound (b), compounds having one or more ethylenic unsaturated groups and compounds having at least one ethylenic unsaturated groups and other functional groups can be used and examples of the compound are the above-mentioned ethylenic unsaturated group-containing compounds and further aromatic vinyl compounds such as an amide type monomer, a (meth) acrylate monomer, an urethane (meth)acrylate oligomer, a polyester (meth) acrylate oligomer, an epoxy (meth) acrylate, and a hydroxyl group-containing (meth)acrylate. Herein, the (meth)acrylate means either acrylate or methacrylate.

Examples of the amide type monomer are amide compounds such as N-vinylpyrrolidone, N-vinylcaprolactam, acryloylmorpholine or the like.

Examples of the (meth)acrylate monomer include imide acrylates such as hexahydrophthalimideethyl acrylate, succimideethyl acrylate or the like; hydroxyalkyl (meth)acrylates such as 2-hydroxyethyl (meth)acrylate, 2-hydroxypropyl (meth)acrylate, 2-hydroxy-3-phenylpropyl acrylate or the like; acrylates of alkylene oxide addition compounds of phenyl and their halogen substituted compounds such as phenoxyethyl (meth)acrylate or the like; glycol mono or di(meth)acrylates such as ethylene glycol mono or di(meth)acrylate, methoxyethylene glycol mono(meth)acrylate, tetraethylene glycol mono or di (meth) acrylate, and tripropylene glycol mono or di (meth) acrylate or the like; (meth)acrylic acid esters of polyols and their alkylene oxides such as trimethylol propane tri (meth) acrylate, pentaerythritol tri (meth) acrylate, pentaerythritol tetra(meth)acrylate, and dipentaerythyritol hexaacrylate or the like; and isocyanuric acid EO-modified di or tri(meth)acrylate or the like.

Examples of the urethane (meth)acrylate oligomer include reaction products obtained by causing reaction of reaction products of polyols and organic polyisocyanates with hydroxyl group-containing (meth)acrylate or the like.

Herein, examples of the polyols include low molecular weight polyols, polyether polyols, polyester polyols or the like. Examples of the low molecular weight polyols are ethylene glycol, propylene glycol, cyclohexane dimethanol, 3-methyl-1,5-pentanediol or the like; examples of the polyether polyols are polyethylene glycol, polypropylene glycol or the like; and examples of the polyester polyols are reaction products of these low molecular weight polyols and/or polyether polyols with acid components of dibasic acids such as adipic acid, succinic acid, phthalic acid, hexahydrophthalic acid, and terephthalic acid and their anhydrides.

Examples of the organic polyisocyanates to be reacted with the above-mentioned polyols include tolylene diisocyanate, 4,4'-diphenylmethane diisocyanate, 4,4'-dicylcohexylmethane diisocyanate, hexamethylene diisocyanate, isophorone diisocyanate or the like.

Examples of the polyester (meth) acrylate oligomer include dehydration condensation products of polyester polyols and (meth)acrylic acid. Examples of the polyester polyols are reaction products of low molecular weight polyols such as ethylene glycol, polyethylene glycol, cyclohexane dimethanol, 3-methyl-1,5-pentanediol, propylene glycol, polypropylene glycol, 1,6-hexanediol, trimethylolpropane or the like and polyols of alkylene oxide addition products of these polyols with acid components of dibasic acids such as adipic acid, succinic acid, phthalic acid, hexahydrophthalic acid, and terephthalic acid and their anhydrides.

Examples of the epoxy (meth)acrylate include compounds obtained by addition reaction of epoxy resins with unsaturated carboxylic acid such as (meth)acrylic acid or the like and practically include epoxy (meth)acrylate of bisphenyl A type epoxy resin, epoxy (meth)acrylate of phenyl or cresol novolac type epoxy resin, and addition reaction products of (meth) acrylic acid with diglycidyl ether, which is a polyether.

The compound having an ethylenic unsaturated group is preferable to have two or more ethylenic unsaturated groups, more preferably 3 or more ethylenic unsaturated groups in terms of three-dimensional crosslinking of the radical polymerizable compounds or radical reactive compounds other than the radical polymerizable compounds.

When the resin composition is used as resist for forming patterns by exposure for electronic parts, color filters or the like, to improve the alkali developing ability of the resin composition, compounds having alkali-soluble or hydrophilic functional groups such as a carboxyl group, a phenylic hydroxyl group, a sulfonic acid group, a hydroxyl group or the like may be used as the compound (b) having an ethylenic unsaturated group.

Also, it is preferable for the radical reactive curable component such as the compound (b) or the like to have no absorption in the wavelength region where the radiation wavelength and the absorption wavelength of the self-cleavage type radical-generating parts are overlapped so as not to interfere the sensitivity of the resin composition to be subjected to the light radiation.

The photosensitive resin composition of the present invention may contain a macro molecular compound or a curable reactive compound having a reaction form other than radical reaction as the binder resin to control the film forming property of the composition put in an uncured state and the physical properties of the coating layer after cured.

As the above mentioned binder resin, any of well known macro molecular compounds and curable reactive compounds having the reaction form other than radical reaction may be used depending on the use of the resin composition. As the macro molecular compounds, non-reactive polymers and polymers having curable reactive groups such as ethylenic unsaturated groups or the like may be used.

Examples, any kinds of well known macro molecular compounds or curable reactive compounds such as organic polyisocyanates, such as tolylene diisocyanate, 4,4'-diphenylmethane diisocyanate, 4,4'-dicylcohexylmethane diisocyanate, hexamethylene diisocyanate, isophorone diisocyanate or the like; polymers and copolymers of acrylic or vinyl compounds such as vinyl acetate, vinyl chloride, acrylic acid ester, methacrylic acid ester or the like; styrene type resin such as polystyrene or the like; acetal resin such as formal resin, butyral resin or the like; silicone resin; phenoxy resin; epoxy resin such as bisphenyl A type epoxy resin or the like; urethane resin such as polyurethane or the like; phenyl resin; ketone resin; xylene resin; polyamide resin; polyimide resin; polyether resin; polyphenylene ether resin; polybenzoxazole resin; cyclic polyolefin resin; polycarbonate resin; polyester resin; polyallylate resin; polystyrene resin; novolac resin; alicyclic polymers such as polycarbodiimide, polybenzoimidazole, polynorbornane or the like; and siloxane type polymers are included.

These macro molecular compounds and curable reactive compounds other than the radical reactive compounds may be used alone or in combination of two or more. The macro molecular compound, which is a binder component, is generally preferable to have a weight average molecular weight of 3,000 or more, although it depends on uses of the resin composition. If the molecular weight is so high, it results in deterioration of the solubility and the processability and therefore, the weight average molecular weight is generally preferable to be 10,000,000 or less.

The amount of the photoradical generator of the present invention in the resin composition is required to be enough to obtain sufficient radical generation amount in order to assure a desirable rate of curing and a high crosslinking density and to improve the strength of the coating layer and the glass transition temperature and from such a viewpoint, the amount of the photoradical generator is preferably 0.1% by weight or more of the total amount of solids in the resin composition. Further, in terms of the radiation sensitivity and physical properties of the coating layer, the amount of the photoradical generator is preferably 1% by weight or more of the total amount of solids in the resin composition.

The solids in the photosensitive resin composition are all components other than the solvent and include liquid phase monomer components.

The compound (b) having an ethylenic unsaturated group is preferably in an amount of 1% by weight of the whole solid content of the resin composition to obtain sufficient photo-curability. The mixing ratio of other radical generator to the compound (b) and other radical reactive compounds may properly be selected depending on the types and amounts of these radical reactive compounds or the uses of the resin composition.

When the binder resin of a macro molecular compound or curable reactive compound other than radical reaction compound is used, the amount is preferably 1% by weight or more and 97% by weight or less in the whole solid content of the resin composition, depending on the uses. If the amount of the binder resin exceeds 97% by weight, curability by light tends to be decreased.

When the resin composition of the present invention is photo-cured, in order to promote radical reaction, if required, other photoradical generators may be used together with the compound (a). When other photoradical generators are used in combination, it is possible to generate decomposition materials by other photoradical generators and cause problems in discoloration or physical properties of the cured film, volatilization of decomposition materials, stability and preserving ability of the resin composition or the like. However, use of the compound (a) in combination can lessen the use amount of other photoradical generators, so that occurrence of the above-mentioned problems is less possible than that in the case of using only other photoradical generators and even if such problems occur, the problems are less serious and therefore, sufficient radical reactivity is exhibited and simultaneously the problems by the photoradical generators can be suppressed to an extent allowable for practical use.

Examples of other photoradical generators to be used include benzoin and its alkyl ethers such as benzoin, benzoin methyl ether, benzoin ethyl ether, benzoin isopropyl ether or the like; acetophenones such as acetophenone, 2,2-dimethoxy-2-phenylacetophenone, 2,2-diethoxy-2-phenylacetophenone, 1,1-dichloroacetophenone, 1-hydroxyacetophenone, 1-hydroxycyclohexyl phenyl ketone, 2-methyl-1-[4-(methylthio)phenyl]-2-morpholino-propan-1-one or the like; anthraquinones such as 2-methylanthraquinione, 2-ethylanthraquinione, 2-tert-butylanthraquinione, 1-chloroanthraquinione, 2-amylanthraquinione or the like; thioxanthones such as 2,4-dimethylthioxanthone, 2,4-diethylthioxanthone, 2-chlorothioxanthone, 2,4-diisopropylthioxanthone or the like; ketals such as acetophenone dimethyl ketal, benzyl dimethyl ketal or the like; monoacylphosphine oxides or bisacylphosphine oxides such as 2,4,6-trimethylbenzoly diphenylphopshine oxide or the like; benzophenones such as benzophenone or the like; and xanthones.

These photoradical generators may be used alone or in combination with benzoic acid type or amine type photopolymerization initiating and promoters. The mixing ratio of these photoradical generators is preferably 0.1% by weight or more to 35% by weight or less, more preferably 1% by weight or more to 10% by weight or less in the whole solid contents of the resin composition.

To provide processability and other various functions to the resin composition of the present invention, various organic and inorganic, low or macro molecular compounds may be added. For example, dyes, surfactants, leveling agents, plasticizers, microparticles, sensitizers and the like can be employed. The microparticles may include organic microparticles such as polystyrene, polytetrafluoroethylene or the like and inorganic microparticles of colloidal silica, carbon, laminar silicates or the like and the functions and forms of them include pigments, fillers, fibers or the like.

The mixing ratio of these optional components is preferably in a range of 0.1 to 95% by weight in the whole solid contents of the resin composition. If it is less than 0.1% by weight, the effects of the added additives are insufficient and if it exceeds 95% by weight, the properties of the resin composition are not well reflected in the final product.

When a large quantity of a component which absorbs radiated light is added, light cannot reach sufficiently to the compound (a), which is a photoradical generator, to result in decrease of the sensitivity. Therefore, from the viewpoint of importance of the sensitivity of the resin composition, the transmittance of the components other than the compound (a) is preferably 20% or more in the wavelength range where the emitting wavelength of the light source and absorption wavelength of the compound (a) added to the resin composition are overlapped.

The resin composition of the present invention may be diluted by using a solvent to a proper concentration. As the solvent, a variety of commonly used solvents may be used and examples are ethers such as diethyl ether, tetrahydrofuran, dioxane, ethylene glycol dimethyl ether, ethylene glycol diethyl ether, propylene glycol dimethyl ether, propylene glycol diethyl ether or the like; glycol monoethers (so-called cellosolves) such as ethylene glycol monomethyl ether, ethylene glycol monoethyl ether, propylene glycol monomethyl ether, propylene glycol monoethyl ether, diethylene glycol monomethyl ether, diethylene glycol monoethyl ether or the like; ketones such as methyl ethyl ketone, acetone, methyl isobutyl ketone, cyclopentanone, cyclohexanone or the like; esters such as ethyl acetate, butyl acetate, n-propyl acetate, iso-propyl acetate, n-butyl acetate, iso-butyl acetate, acetic acid esters of the above-mentioned glycol monoethers (e.g. methyl cellosolve acetate and ethyl cellosolve acetate), methoxypropyl acetate, ethoxypropyl acetate, dimethyl oxalate, methyl lactate, ethyl lactate or the like; alcohols such as ethanol, propanol, butanol, hexanol, cyclohexanol, ethylene glycol, diethylene glycol, glycerin or the like; halo hydrocarbons such as methylene chloride, 1,1-dichloroethane, 1,2-dichloroethylene, 1-chloropropane, 1-chlorobutane, 1-chloropetane, chlorobenzene, bromobenzene, o-dichlorobenzene, m-dichlorobenzene or the like; amides such as N,N-dimethylformamide, N,N-dimethylacetamide or the like; pyrrolidones such as N-methylpyrrolidone or the like; lactones such as γ-butyrolactone or the like; sulfoxides such as dimethyl sulfoxide or the like; and other organic polar solvents as well as aromatic hydrocarbons such as benzene, toluene, xylene or the like and other organic non-polar solvents or the like. Further, as a reactive diluent, compounds having reactive groups such as ethylenic unsaturated compounds in liquid state at a normal temperature may also be used as solvents. These solvents may be used alone or in combination. These solvents may be used after being filtered by known various methods with, for example, a filter having a pore diameter of 0.05 μm to 0.2 μm to remove impurities.

The resin composition can be produced by mixing the photoradical generator, which is an essential component with, if required, a curable reactive compound such as the compound (b) having an ethylenic unsaturated group or the like, optional components such as high molecular weight binder components and the like by stirring the mixture or the like depending on the occasions and uses.

The resin composition of the present invention obtained in such a manner can be used for all of the known fields and products, for which materials curable or changeable in solubility by light radiation are utilized, such as pattern-forming materials (resist), coating materials, paints, printing inks, adhesives, fillers, electronic materials, molding materials, three-dimensional articles or the like. Particularly, it is suitable for those which are required heat resistance and a high reliability, such as forming paints, printing inks, color filters, electronic parts, layer insulation films, wire cover films, optical members, optical circuits, optical circuit parts, antireflection films, holograms or building materials.

In the case of, for example, the color filter, a pixel portion, light-shading portion (black matrix) disposed at a boundary of pixels, a protective layer and a spacer for keeping a cell gap may be formed of a cured product of the above described photosensitive resin composition.

In the case of the electronic parts, an under-filling agent, a sealing agent or the like used in semiconductor devices may be exemplified.

As to the layer insulation films, layer insulation films for build-up substrates, layer insulation films in fuel cells and insulation coatings of car parts or domestic electric products, for which the heat resistance and the reliability to insulation are required, may be formed of a cured product of the photosensitive resin composition.

Also, as the wire protective films, solder resists which are wire protective layers on the surface of printed boards, wire surface covers or the like may be exemplified.

In the case of the optical members, overcoats of various optical lenses, antireflection films, optical waveguides, optical circuit parts such as wave dividers or the like, relief type or volume type holograms or the like may be exemplified.

In the case of the building materials, wall papers, wall materials, floor materials and other surface covering materials reduced in volatile components, adhesives/pressure sensitive adhesives and inks may be exemplified.

The print product, color filter, electronic parts, layer insulation film, wire cover film, optical member, optical circuit, optical circuit parts, antireflection film, hologram or building material according to the present invention has high heat resistance and stability and therefore has such a merit that productive yield is high since at least a part of each is formed of a cured product of the photosensitive resin composition having high heat resistance and stability.

EXAMPLE

Example 1

500 ml eggplant type flask was loaded with 5 g of LUNA 750 (product name: manufactured by Nihon Siber Hegner K.K.), which is a mixture obtained by modifying benzophenone portion of α-aminoacetophenone with a plurality of caprolactone molecules, 12.5 g of 4-dimethylaminopyridine (DMAP) and 300 ml of dried toluene, and the mixture was stirred. 3 ml of acrylic acid chloride was dropwise added to the mixture and stirred at a room temperature for 1 hour. After that, 1 ml of acrylic acid chloride was dropwise added after every 1 hour until no spot of the raw materials was found in the resulting reaction solution by thin layer chromatography. On completion of the reaction, after the reaction solution was treated with distilled water and a saturated sodium hydrogencarbonate aqueous solution by a separating funnel, the organic solvent layer was dehydrated by magnesium sulfate and the solvent was removed by distillation with a rotary evaporator. The obtained reaction solution was refined by column chromatography to obtain a compound 1 represented by the following formula (5). The compound 1 has a structure in which hexamer caprolactone-modified portion having acryloyl group introduced at the end is extended from the benzoyl group side of the radical generation portion:

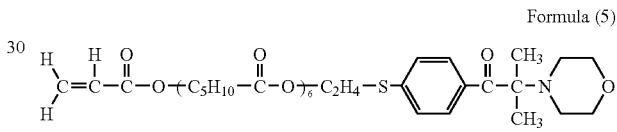

Formula (5)

Example 2

A mixture containing a raw material compound (A) represented by the following formula (6) as a main component and a compound having the same basic skeleton and differing in the number of the repeating units of the caprolactone-modified portion was used in place of LUNA 750 in Example 1 and reacted with acrylic acid chloride, and the obtained reaction product was refined in the same manner as Example 1 to obtain a compound 2 represented by the following formula (7). The compound 2 has a structure formed by introducing an acryloyl group into the end of trimer caprolactone-modified portion of the compound (A):

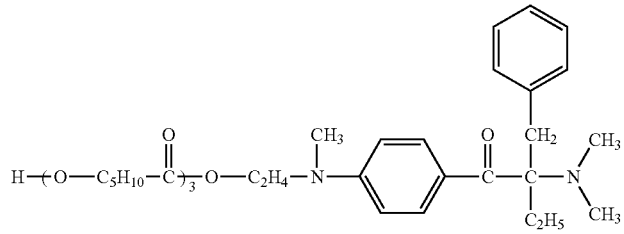

Formula (6) : raw material

-continued

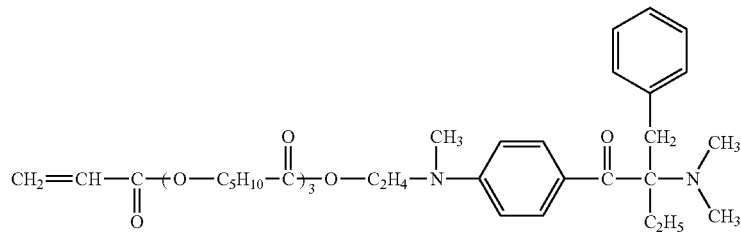

Formula (7) : compound 2

Example 3

A mixture containing a raw material compound (B) represented by the following formula (8) as a main component and a compound having the same basic skeleton and differing in the number of the repeating units of the caprolactone-modified portion was used in place of LUNA 750 in Example 1, and reacted with acrylic acid chloride and the obtained reaction product was refined in the same manner as Example 1 to obtain a compound 3 represented by the following formula (9). The compound 3 has a structure formed by introducing an acryloyl group into the end of trimer caprolactone-modified portion of the compound (B):

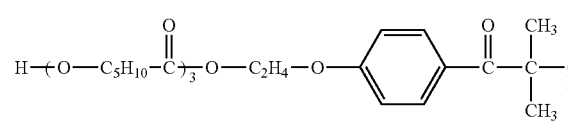

Formula (8) : raw material

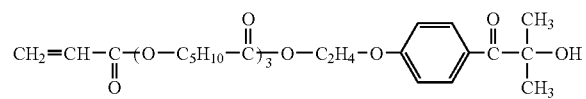

Formula (9) : compound 3

Example 4

A mixture containing a raw material compound (C) represented by the following formula (10) as a main component and a compound having the same basic skeleton and differing in the number of the repeating units of the caprolactone-modified portion was used in place of LUNA 750 in Example 1 and reacted with acrylic acid chloride, and the obtained reaction product was refined in the same manner as Example 1 to obtain a compound 4 represented by the following formula (11). The compound 4 has a structure formed by introducing an acryloyl group into the end of trimer caprolactone-modified portion of the compound (C):

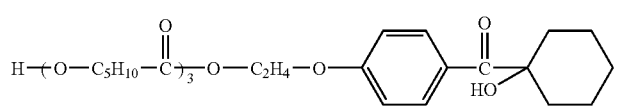

Formula (10) : raw material

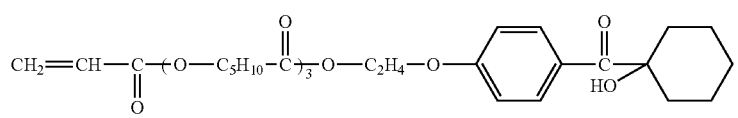

Formula (11) : compound 4

2. Evaluation Test (1) Evaluation of Heat Resistance

Using a differential type differential thermal balance (product name: TG8120; manufactured by Rigaku Corporation), the 5% reduction in weight temperature of the compound 1 was measured at a temperature rise rate of 10° C./min in nitrogen atmosphere. As comparative examples, same measurement was carried out for LUNA 750 (trade name; manufactured by Nihon Siber Hegner K.K.) and Irgacure 907 (trade name; manufactured by Ciba Specialty Chem. Corp.). Both of LUNA 750 and Irgacure 907 are self-cleavage type photoradical initiators. Particularly, LUNA 750 is the raw material of the compound 1 and has a structure in which the caprolactone-modified portion is extended from the benzoyl group side of the radical generation part.

The 5% reduction in weight temperatures of the compound 1 and the respective comparative compounds are shown in Table 1. As compared with LUNA 750 and Irg907 having photopolymerization initiating parts with the same skeleton, it was found that the compound 1 considerably improved the 5% reduction in weight temperature owing to the introduction of acryloyl group. According to this result, it was found that the heat resistance was improved and the production of volatile components by heating could be considerably decreased by introducing an acryloyl group into the self-cleavage type photoradical generator.

TABLE 1

| | 5% reduction in weight temperature (° C.) |
|---|---|
| Compound 1 | 330 |
| LUNA 750 | 192 |
| Irg907 | 207 |

(2) Curability Evaluation

Trifunctional pentaerythritol triacrylate (PETA) (product name; M305, manufactured by Toagosei Co., Ltd.) as a polyfunctional monomer was mixed with the compounds 1 to 4, LUNA 750 (product name; manufactured by Nihon Siber Hegner K.K.), and Irgacure 907 (product name; manufactured by Ciba Specialty Chem. Corp.) at a ratio proper to adjust the mole ratio of the photoradical generator portions of each example to the double bonds of the polyfunctional monomer to be 1/50, thus, THF solutions of the respective mixtures were produced. Each solution was spin-coated on a glass substrate, which was treated by chromium sputtering, to form a coating layer. A coating layer containing only the trifunctional acrylate and no initiator component was formed as a blank.

While each coating layer was exposed by UV, a decrement of the peak at 810 cm$^{-1}$ was recorded with time by using an infrared spectrometer (product name: FTS6000; manufactured by BIO RAD) to confirm how much the double bond elimination was promoted. The atmosphere surrounding each sample was replaced with nitrogen at the time of measurement. As the UV exposure apparatus, UV Spot Cure SP-III type (standard reflecting mirror type) manufactured by Ushio Inc. was used and as the UV lamp, USH-255BY (manufactured by Ushio Inc.) was used.

The results of observing compatibility of each sample with trifunctional acrylate M305, odor at the time of exposure, the decrease amount (reaction ratio) of the double bonds to the exposure, and coloring of each coating layer are shown in Table 2.

TABLE 2

| | Compatibility with M305 | Odor during exposure | Reaction ratio (%) Exposure [mJ] | | | Coloring in coating layer |
|---|---|---|---|---|---|---|
| | | | 50 | 100 | 400 | |
| Compound 1 | ○ | No | 51.8 | 56.8 | 64.5 | Brown |
| 2 | ○ | No | 33.1 | 41.1 | 47.6 | Yellow |
| 3 | ○ | No | 10.3 | 19.9 | 32.1 | Pale yellow |
| 4 | ○ | No | 12.1 | 22.2 | 36.3 | Pale yellow |
| LUNA 750 | ○ | No | 55.1 | 60.7 | 69.7 | Brown |
| Irg907 | ○ | Yes | 34.8 | 40.8 | 50.6 | Yellow |

According to the results, although being decreased slightly by introduction of an acryloyl group as compared with that of LUNA 750, the reaction ratio of the compound 1 was improved as compared with that of Irgacure 907 and thus found having good sensitivity. The higher reaction ratio of the compound than that of Irgacure 907 having similar radical generating parts was supposedly because of flexible skeleton of the caprolactone portion which is a side chain introduced into the skeleton of the compound 1 and LUNA 750 so that the fluidity of the coating layer was increased and the mobility of the radicals and reactive groups was improved.

Although the compounds 1 and 2 had high degree in coloring of coating layers, they had high sensitivity and therefore they are suitable for the cases which high sensitivity is required and the compounds 3 and 4 had slight coloring in coating layers although having relatively low sensitivity, and therefore they are supposed to be suitable for uses required to be highly transparent.

(3) Outgas Test

The compound 1 and pentaerythritol triacrylate (PETA) (trade name: M305, Toagosei Co., Ltd.) were mixed at a ratio adjusted so as to keep the mole ratio of the double bonds of the compound 1 and the double bonds of PETA at 1/50 (=compound 1/PETA) and diluted with chloroform so as to adjust the solids in an amount of 20 wt % (photosensitive resin composition 1) Photosensitive resin compositions 2 to 4 were also prepared in the same manner by using the compounds 2 to 4 in place of the compound 1.

Each of the above-mentioned photosensitive resin compositions 1 to 4 was spin-coated on a glass substrate and heated at 50° C. for 1 minute on a hot plate and exposed at 2,000 mJ/cm$^2$ based on the conversion into h ray by a high pressure mercury lamp using a manual exposure apparatus (MA-1200; manufactured by Dainippon Screen Co., Ltd.) to form a coating layer having thickness of 25 μm.

A photosensitive resin composition was prepared using Irgagure 907 and a coating layer was obtained in the same manner as a comparative example.

Each glass substrate coated with the coating layer was cut into 1 cm×1.5 cm size and the gas emitted when heated at 250° C. for 1 hour was analyzed by GC-MS (QP-5000; manufactured by Shimadzu Corporation). Other measurement conditions were as follows:

Collection apparatus: Curie Point Purge and Trap (JHS-100A model; manufactured by Nippon Bunseki Kogyo Co., Ltd.);
Heating condition: 250° C.×60 min;
Adsorbent: TENAX TA (2,6-diphenyl-p-phenylene oxide) weak polarity;
Collection temperature: −40° C. (using liquefied nitrogen for cooling);
Thermal decomposition temperature: 255° C.×30 s;
Injection temperature: 250° C.;
Column: 5% phenyl-95% dimethyl siloxane (PTE-5) slight polarity, inner diameter: 0.25 μm, length: 30 m;
Column temperature: 50° C.×5 min (holding), 10° C./min (temperature increase), 320° C.×3 min (holding);
Ionization method: electron bombardment ionization (EI method); and
Detector: quadruple detector.

According to the result of the outgas test, decomposition materials derived from the polyfunctional monomer M-305 were detected for all of the samples using the compounds 1 to 4 and Irgacure 907.

As the outgas component derived from the initiator from the coating layer formed by using the compound 1, a slight amount of a compound having morpholine skeleton was detected, however no compound having aromatic ring was detected. On the other hand, as the outgas component derived from the initiator from the coating layer formed by using Irgacure 907, in addition to a slight amount of the compound having morpholine skeleton, compounds having aromatic rings such as benzaldehyde and acetophenone were detected.

For the case of using the compounds 3 and 4, no aromatic compound was detected as the outgas component. For the case of using the compound 2, although aromatic compounds were detected, benzaldehyde and acetophenone were not detected.

According to the above-mentioned facts, the compounds of the present invention were found effective to suppress particularly components containing aromatic ring, which become causes of odor, in outgas derived from initiators.

What is claimed is:

1. A photoradical generator comprising a compound (a1) represented by the following formula (1):

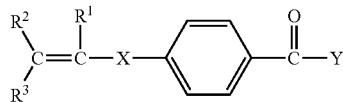

Formula (1)

wherein $R^1$, $R^2$ and $R^3$ respectively represent a hydrogen atom, a halogen atom or a monovalent organic group; X represents a divalent group; and Y represents a monovalent group having an aliphatic tertiary amine structure.

2. A photoradical generator according to claim 1, wherein X comprises sulfur bonded to the benzoyl structure of formula (1).

3. A photoradical generator according to claim 1, wherein a 5% reduction in weight temperature is 50° C. or more.

4. A photoradical generator according to claim 1, wherein the compound (a1) is represented by the following formula (2):

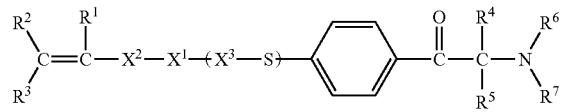

(2)

wherein $R^1$, $R^2$ and R3 respectively represent a hydrogen atom, a halogen atom, or a monovalent organic group; $R^4$ and $R^5$ respectively represent a hydrogen atom or an alkyl having 1 to 15 carbon atoms; $R^6$ and $R^7$ respectively represent a monovalent organic group and may have hetero atoms such as O, N, S, Si or the like other than C; $R^6$ and $R^7$ may be bonded to each other to form a ring structure; $X^1$ represents a divalent organic group; and, $X^2$ and $X^3$ independently represent a divalent group.

5. A photoradical generator according to claim 1, wherein the aliphatic tertiary amine structure of formula (1) has a morpholine skeleton.

6. A photoradical generator comprising a compound (a1') represented by the following formula (3):

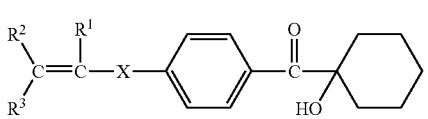

(3)

wherein $R^1$, $R^2$ and $R^3$ respectively represent a hydrogen atom, a halogen atom or a monovalent organic group; X represents a divalent group; and, X contains oxygen bonded to the benzoyl structure.

* * * * *